US011937905B2

(12) United States Patent
Singleton et al.

(10) Patent No.: US 11,937,905 B2
(45) Date of Patent: Mar. 26, 2024

(54) TECHNIQUES FOR LEVERAGING DATA COLLECTED BY WEARABLE DEVICES AND ADDITIONAL DEVICES

(71) Applicant: Oura Health Oy, Oulu (FI)

(72) Inventors: Robert Alexander Singleton, Toronto (CA); Steve Kent, San Francisco, CA (US); Mika Erkkilä, Oulu (FI); Heli Tuulia Koskimäki, Oulu (FI); Michael Chapp, Lafayette, CA (US)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 18/087,582

(22) Filed: Dec. 22, 2022

(65) Prior Publication Data

US 2023/0210395 A1 Jul. 6, 2023

Related U.S. Application Data

(60) Provisional application No. 63/295,134, filed on Dec. 30, 2021.

(51) Int. Cl.
*A61B 5/026* (2006.01)
*A61B 5/00* (2006.01)

(52) U.S. Cl.
CPC ............ *A61B 5/026* (2013.01); *A61B 5/6826* (2013.01); *A61B 5/7435* (2013.01)

(58) Field of Classification Search
CPC ..... A61B 5/026; A61B 5/6826; A61B 5/7435; A61B 5/0022; A61B 5/01; A61B 5/02055; A61B 5/1112; A61B 5/1118; A61B 5/6803; A61B 5/681
See application file for complete search history.

(56) References Cited

U.S. PATENT DOCUMENTS

2020/0077942 A1\* 3/2020 Youngblood ...... A61B 5/02055

OTHER PUBLICATIONS

International Search Report and Written Opinion—PCT/US2022/082344—ISA/EPO—dated Apr. 28, 2023.

\* cited by examiner

*Primary Examiner* — Eric F Winakur
*Assistant Examiner* — Abid A Mustansir
(74) *Attorney, Agent, or Firm* — Holland & Hart LLP

(57) ABSTRACT

Methods, systems, and devices for leveraging data from multiple data sources are described. A method includes receiving physiological data associated with a user from a wearable device and receiving additional data from an external device different from the wearable device, the additional data including at least data associated with characteristics of an environment associated with the user. The method further includes identifying one or more relationships between the collected physiological data and the characteristics of the environment associated with the user, and causing a graphical user interface (GUI) of a user device to display an indication of the one or more relationships, a message associated with the one or more relationships, or both. In some cases, the method includes causing the GUI to display instructions for selectively adjusting the one or more characteristics of the environment associated with the user based on the one or more relationships.

20 Claims, 10 Drawing Sheets

TECHNIQUES FOR LEVERAGING DATA COLLECTED BY WEARABLE DEVICES AND ADDITIONAL DEVICES

CROSS REFERENCE

The present Application for Patent claims the benefit of U.S. Provisional Patent Application No. 63/295,134 by Singleton et al., entitled "TECHNIQUES FOR LEVERAGING DATA COLLECTED BY WEARABLE DEVICES AND ADDITIONAL DEVICES," filed Dec. 30, 2021, assigned to the assignee hereof and expressly incorporated by reference herein.

FIELD OF TECHNOLOGY

The following relates to wearable devices and data processing, including techniques for leveraging data collected by wearable devices and additional devices.

BACKGROUND

Some wearable devices may be configured to collect data from users associated with a heart rate of the user, such as motion data, temperature data, photoplethysmogram (PPG) data, etc. However, some users have a desire for more insight regarding their physiological data.

DETAILED DESCRIPTION

Figure 1:
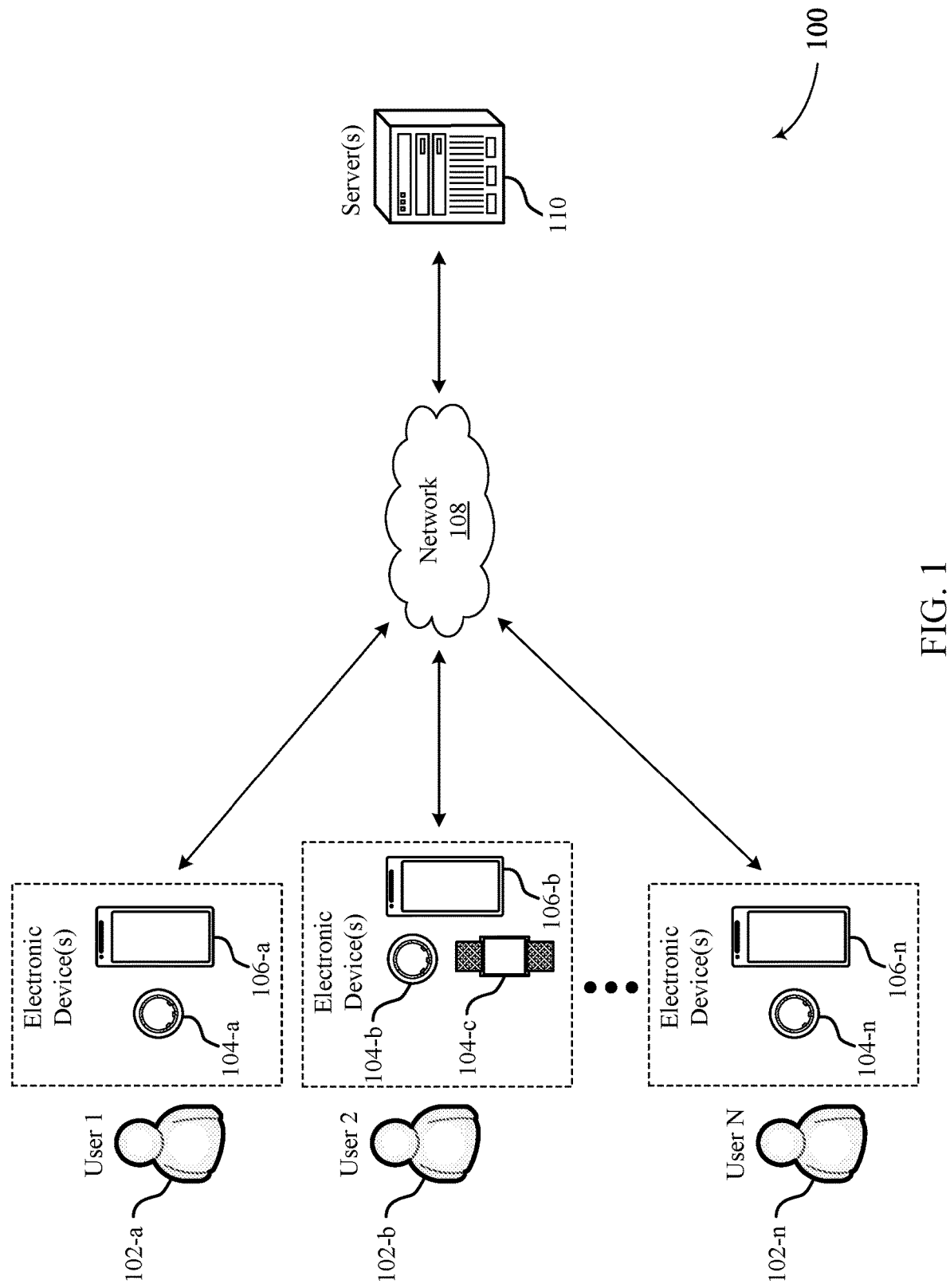
FIG. 1 illustrates an example of a system that supports techniques for leveraging data collected by wearable devices and additional devices in accordance with aspects of the present disclosure.

A user may use a device (e.g., a wearable device) to determine physiological measurements of the user, such as temperature, heart rate, respiratory rate, photoplethysmography (PPG) data, and the like. Physiological data collected via a wearable device may be used to gain insights into the user's sleeping patterns and overall health. For example, motion data and temperature data may be used to evaluate a user's sleep to determine how restful the sleep is, and how beneficial (or detrimental) the user's sleep is to their overall health.

However, at face value, physiological data collected via wearable devices may only be used to determine if/when a user exhibits health related issues. That is, in some cases, physiological data on its own may not be enough to inform users as to potential causes for their physiological data trends, including how the user's surrounding environment may affect their physiological data and overall health. For example, a wearable device may be able to inform the user that they are receiving poor sleep that is negatively affecting their overall health, but may not be able to inform the user as to what is causing the poor sleep, or how they may adjust their sleeping patterns, surroundings, or behavioral characteristics to achieve higher quality sleep.

Accordingly, aspects of the present disclosure are directed to systems and methods that utilize physiological data collected via wearable devices, as well as additional data collected from other devices, to gain better insights into the user's overall health. In particular, aspects of the present disclosure may leverage data from multiple data sources (e.g., physiological data from wearable devices, additional data from external devices) to identify relationships (e.g., physiological relationships) between a user's physiological data and their surrounding environment in order to provide more accurate and helpful guidance to the user regarding their behavioral characteristics and overall health. In this regard, aspects of the present disclosure may be used to determine how a user's surrounding environment (e.g., surrounding temperature, pressure, humidity, noise, sound, air quality) affects the user's overall health, and to provide targeted guidance to the user as to how they may adjust their surroundings to improve their overall health.

In some implementations, data from other, external devices may be used to identify relationships (e.g., physiological relationships, positional relationships) between a user and the respective external device. Such relationships between the user and the external devices may be further used to derive health-related insights between the user's physiological data and their surrounding environment, and to provide more pertinent, targeted guidance to the user. For example, a system of the present disclosure may collect data from a user device (e.g., smartphone) associated with the user and a virtual assistant device in the user's kitchen. In this example, the system may be configured to identify that the user is likely located in the kitchen based on a Bluetooth or other wireless connection formed between the user device and the virtual assistant device, and may provide kitchen-related notifications or messages to the user. For instance, the system may display a message that reminds the user to take their vitamins that are likely stored in the kitchen. By leveraging data from external devices (e.g., user device, smart appliance, virtual assistance device, voice-activated smart device, home monitoring device), the system may be able to more accurately identify the user's position, and provide guidance/messages to the user based on the user's determined position.

In additional or alternative implementations, data from other devices may be used to identify relationships between a user and their surroundings. For example, by collecting data from electronic devices associated with other users (e.g., user devices, wearable devices), aspects of the present disclosure may be used to perform a form of "contact tracing" by identifying potential interactions between a user and other users (e.g., based on wireless connections formed between user devices associated with different users). In some implementations, physiological data collected during/proximate to potential interactions between users may be used to evaluate a relative characteristic of the interaction (e.g., positive interaction, negative interaction, neutral interaction), and to evaluate how a user's physiological data is affected by interactions with particular users, groups of users, etc.

Aspects of the disclosure are initially described in the context of systems supporting physiological data collection from users via wearable devices. Aspects are then described with reference to an example graphical user interface (GUI). Aspects of the disclosure are further illustrated by and described with reference to apparatus diagrams, system diagrams, and flowcharts that relate to techniques for leveraging data collected by wearable devices and additional devices.

FIG. 1 illustrates an example of a system 100 that supports techniques for leveraging data collected by wearable devices and additional devices in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, that may measure physiological parameters and some of that may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof. In general, the terms light-emitting components, light-emitting elements, and like terms, may include, but are not limited to, LEDs, micro LEDs, mini LEDs, laser diodes (LDs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for leveraging physiological data collected via wearable devices 104, as well as additional data collected from other devices (e.g., user devices 106, chargers for the wearable devices 104), to gain better insights into the user's overall health. In particular, the respective devices of the system 100 may support techniques for leveraging data from multiple data sources (e.g., physiological data from wearable devices 104, additional data from external devices) to identify relationships between a user's physiological data and their surrounding environment in order to provide more accurate and helpful guidance to the user 102 regarding their behavioral characteristics and overall health. In this regard, aspects of the present disclosure may be used to determine how a user's surrounding environment (e.g., surrounding temperature, pressure, humidity, noise, sound, air quality) affects the user's overall health, and to provide targeted guidance to the user 102 as to how they may adjust their surroundings to improve their overall health.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
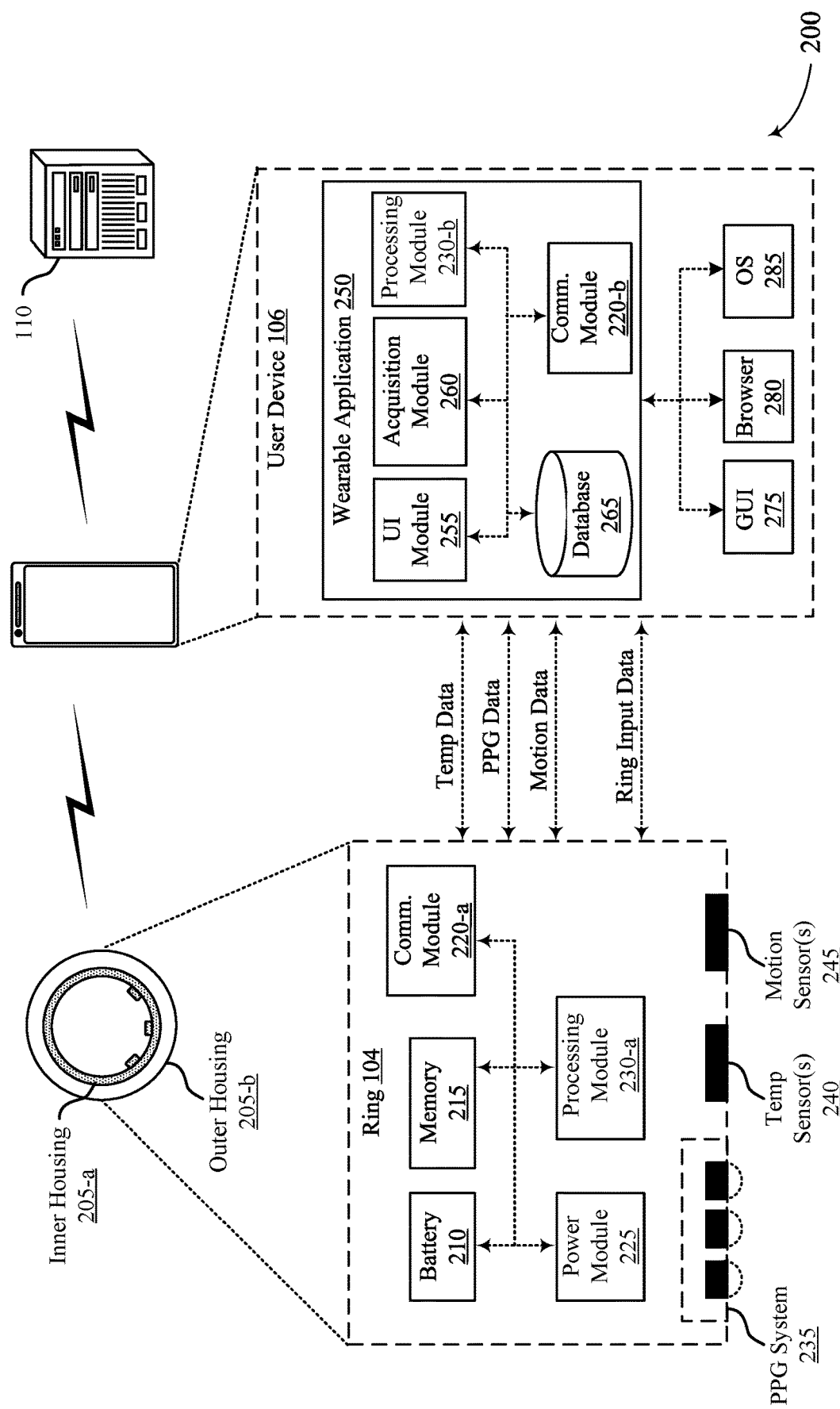
FIG. 2 illustrates an example of a system that supports techniques for leveraging data collected by wearable devices and additional devices in accordance with aspects of the present disclosure.

FIG. 2 illustrates an example of a system 200 that supports techniques for leveraging data collected by wearable devices and additional devices in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205, that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, which may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-a. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, where the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform, that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for leveraging physiological data collected via wearable devices 104, as well as additional data collected from other devices (e.g., user devices 106, chargers for the wearable devices 104), to gain better insights into the user's overall health. In particular, the respective devices of the system 100 may support techniques for leveraging data from multiple data sources (e.g., physiological data from wearable devices 104, additional data from external devices) to identify relationships between a user's physiological data and their surrounding environment in order to provide more accurate and helpful guidance to the user 102 regarding their behavioral characteristics and overall health. In this regard, aspects of the present disclosure may be used to determine how a user's surrounding environment (e.g., surrounding temperature, pressure, humidity, noise, sound, air quality) affects the user's physiological data and overall health, and to provide targeted guidance to the user 102 as to how they may adjust their surroundings and improve their overall health.

For example, as noted previously herein, the ring 104 of the system 200 may be worn by a user 102 to collect physiological data from the user 102, including temperature data, heart rate data, respiratory rate data, movement data, PPG data, and the like. The ring 104 of the system 200 may collect the physiological data from the user 102 based on arterial blood flow. Moreover, the system 200 may be configured to leverage data collected from external devices in order to provide context for the collected physiological data, determine relationships between the user's physiological data and their surrounding environment, and provide more helpful and insightful guidance for the user 102.

Figure 3B:
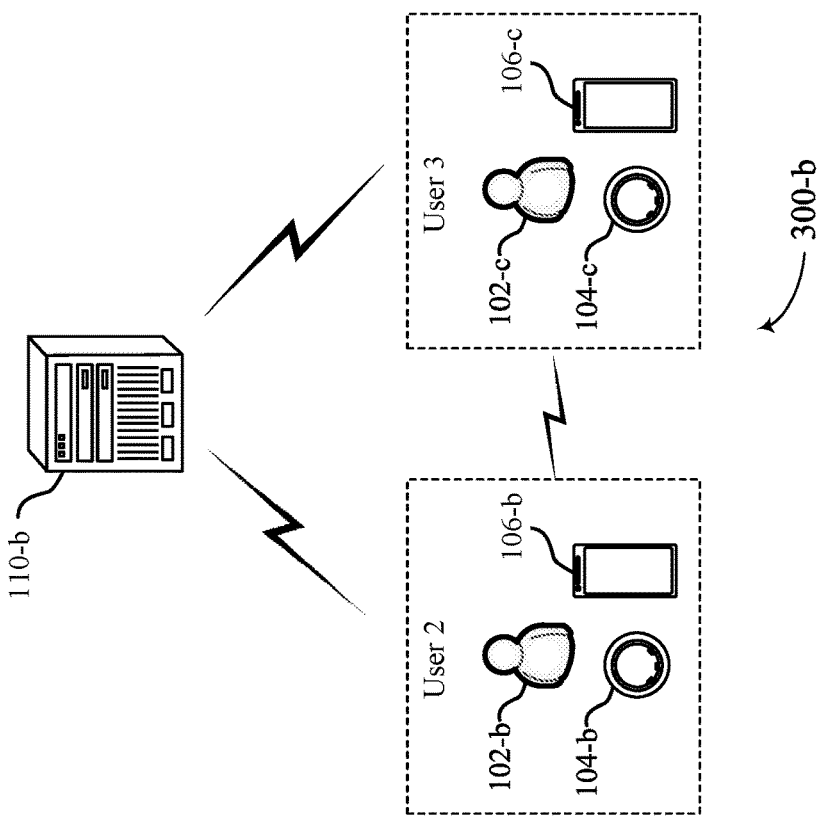
FIGS. 3A and 3B illustrate examples of systems that support techniques for leveraging data collected by wearable devices and additional devices in accordance with aspects of the present disclosure.
Figure 3A:
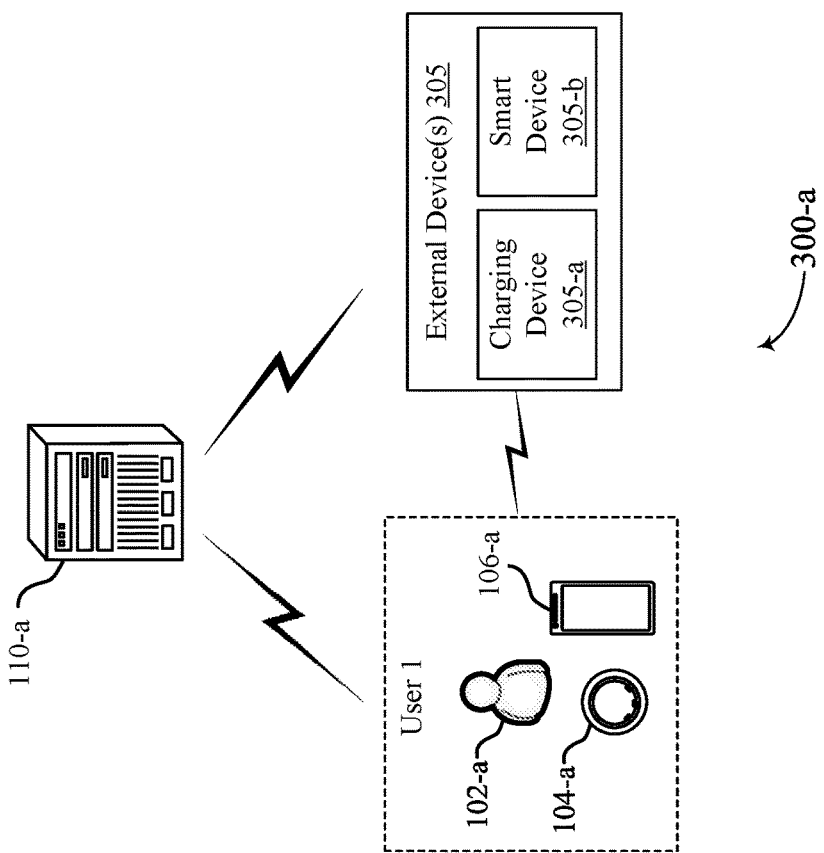

Attendant advantages of the present disclosure may be described in further detail with respect to FIGS. 3A and 3B.

FIGS. 3A and 3B illustrate examples of systems 300-a and 300-b that support techniques for leveraging data collected by wearable devices and additional devices in accordance with aspects of the present disclosure. Aspects of systems 300-a and 300-b may implement, or be implemented by, aspects of the system 100, system 200, or both. In particular, systems 300-a and 300-b illustrate examples of external devices that may be used to collect additional data that may be used to identify relationships between a user's physiological data and their surrounding environment.

As shown in FIG. 3, the system 300-a may include a user 102-a associated with a wearable device 104-a and a user device 106-a, a server 110-a, and one or more external devices 305. In some aspects, the wearable device 104-a may be configured to acquire physiological data associated with the user. Additionally, the one or more external devices 305 and the user device 106-a (that may include an example of an "external device 305" in some examples) may be configured to collect additional data that may be used to evaluate relationships between physiological data collected from the user 102-a and a surrounding environment associated with the user 102-a.

In general, the term "external device" may be used to refer to any external device other than the wearable device 104-a that may be used to collect additional data that may be used by the system 300-a to gain further insights regarding the user's overall health. For example, in some implementations, the user device 106-a may include an example of an external device 305. By way of another example, as shown in FIG. 3, the one or more external devices 305 may include a charging device 305-a (e.g., charging device configured for charging the wearable device 104-a and/or user device 106-a), smart devices 305-b (e.g., smart lights, smart speakers, virtual assistant device, voice-activated smart device, smart display, streaming device, thermostat, smoke detector, routers, security systems, smart locks, etc.), and the like. In some aspects, data collected via external devices 305 (e.g., user device 106-a, charging device 305-a, smart devices 305-b) may be leveraged, in addition to physiological data collected via the wearable device 104-a, to gain more relevant and informative insights regarding the user's overall health.

For example, the user 102-a may charge the wearable device 104-a with the charging device 305-a that is positioned next to the user's bed. In this example, the charging device 305-a may include one or more sensors configured to collect data, including temperature sensors, noise sensors, light sensors, humidity sensors, air quality sensors, and the like. In this example, the system 300-a (e.g., user device 106-a, server 110-a) may be configured to collect physiological data collected via the wearable device 104-a and additional data collected via the charging device 305-a in order to identify relationships between the collected physiological data and one or more characteristics of the user's surrounding environment. In this regard, the system 300-a may be configured to determine how the user's surrounding environment (e.g., surrounding temperature, humidity, noise levels, ambient light levels, air quality metrics, air pressure metrics) affects their sleep and physiological data, and to identify characteristics that positively or negatively affect the user's sleep or overall health.

Other examples of external devices 305 that may be implemented within the systems 300 may include, but are not limited to, smart/adjustable beds (e.g., beds able to change angles, firmness, temperature), sound machines (e.g., white noise machines), and the like. In such cases, the system 300 may acquire data from the adjustable bed (e.g., bed incline/decline settings, firmness settings temperature settings) and/or the sound machine (e.g., sound type, volume settings), and may compare the collected data to the user's physiological data to determine what settings of the adjustable bed and/or sound machine positively or negatively affect the user's sleep quality or other physiological parameters. In this regard, the system 300 may be able to make recommendations for the user to adjust settings of the adjustable bed and/or sound machine, or may be configured to automatically make such adjustments (e.g., by transmitting a signal from the user device 106 to the adjustable bed/sound machine).

In some aspects, relationships between the user's collected physiological data and the one or more characteristics of the environment associated with the user 102-a may be displayed to the user 102-a via the user device 106-a (e.g., via a GUI of the user device 106-a. For example, based on temperature data collected via the charging device 305-a, the system 300-a may determine that the user 102-a receives poor sleep when the temperature of the user's room raises above 71° F., and may display a message indicating the identified relationship via the user device 106-a. Messaging and other indications that may be displayed to the user 102 are described in further detail herein with respect to FIG. 4.

In some aspects, the systems 300-*a*, 300-*b* may display messages or other guidance that instruct the user 102 to selectively adjust characteristics of their surrounding environment. In particular, the systems 300 may provide guidance based on determined relationships between the user's physiological data and their surrounding environment. For example, continuing with the same example from above, the system 300-*a* may display a message (e.g., via the user device 106-*a*) that instructs the user 102-*a* to lower the temperature in their bedroom to less than 71° F. in order to achieve better sleep.

In some cases, data collected via external devices 305 (e.g., user device 106-*a*, charging device 305-*a*, smart device 305-*b*) may be used to more accurately identify a position of the user 102-*a*. In particular, data collected from devices other than the wearable device 104 may be used to identify a positional relationship between the user 102-*a* and other users 102/other devices, where the positional relationship may be used to provide tailored guidance/messaging to the user 102-*a*, and further gain further insight regarding the relationship between the user 102-*a* and their surrounding environment.

For example, upon walking into the kitchen, the user device 106-*a* and/or wearable device 104-*a* may establish a wireless connection (e.g., Bluetooth connection) with a virtual assistant device (e.g., smart device 305-*b*) positioned within the kitchen. In this example, the user device 106-*a*, the smart device 305-*b*, or both, may store data associated with the wireless connection, and may transmit stored data to the user device 106-*a*, the server 110-*a*, or both. As such, in this example, the user device 106-*a* and the virtual assistant device (e.g., smart device 305-*b*) may be considered as "external devices" that collect additional data used to evaluate relationships between the user's physiological data and their surrounding environment.

Continuing with the same example, the system 300-*a* (e.g., user device 106-*a*, server 110-*a*) may identify a positional relationship between a first position of the user 106-*a* and a second position of the virtual assistant device (e.g., smart device 305-*b*) based on the data received from the user device 106-*a* and/or smart device 305-*b*. In other words, the system 300-*a* may determine that the user 102-*a* is likely positioned within the kitchen based on the wireless connection (e.g., Bluetooth connection) that was established between the user device 106-*a* and the smart device 305-*b*.

In some implementations, the system 300-*a* may display a message to the user 102-*a* (e.g., via a GUI of the user device 106-*a*) based on identified positional relationships for the user 102-*a*. For example, upon determining a positional relationship that indicates the user 102-*a* is likely in their kitchen, the system 300-*a* may cause the user device 106-*a* to display a message reminding the user 102-*a* to take their vitamins that are likely stored in the kitchen. In this regard, aspects of the present disclosure may be used to provide more tailored, target guidance/messaging to the user 102-*a* based on the user's position, that may increase the likelihood that the user 102-*a* will positively act in accordance with (e.g., in response to) the guidance/messaging.

In some implementations, the user device 106-*a* may serve as an external device where data may be acquired to determine relationships (e.g., positional relationships, potential interactions) between the user 102-*a* and the user's surrounding environment. Additional data may be collected and utilized from the user device 106-*a* and may include data collected/generated via one or more applications executable on the user device 106-*a*, including a calendar application, a mail application, a messaging application, a weather application, flight itineraries, a camera application (e.g., when using the camera application, the user's heart rate lowers for a positive impact), a maps/navigation application (e.g., a user's physiological data changes depending on GPS location/altitude), a phone application (e.g., how phone calls with certain people, or quantity of phone calls, affects the user's physiological data), a fitness/health application (e.g., data from fitness apps may be used to improve calculations of user physiological data or give extra data that ring does not measure), media applications (e.g., listening to specific music may affect the user's physiological data), and the like.

For example, the system 300-*a* may collect physiological data associated with the user 102-*a* via the wearable device 104-*a*, and may acquire additional data via the user device 106-*a*. The additional data may include any data or information associated with the user 102-*a*, the user's surrounding environment, and the like. For example, the additional data may include data associated with past or upcoming travel plans for the user 102-*a*, an upcoming time zone change for the user 102-*a* (e.g., upcoming time zone change corresponding to an upcoming vacation), a Daylight Savings time shift, or any combination thereof. In this example, the system 300-*a* may identify or predict a relationship between the user's physiological data and the additional data, and may display instructions for adjusting behavioral characteristics of the user 102-*a* based on the identified relationship. For instance, the system 300-*a* may identify that the user 102-*a* will be traveling to a different time zone, and may thereby instruct the user 102-*a* (e.g., via a GUI of the user device 106-*a*) to adjust the user's sleep schedule to properly prepare for the upcoming time zone change, jetlag, etc.

By way of another example, the system 300-*a* may leverage data from the user device 106-*a* to determine a geographical position, latitude, and/or altitude of the user, such as via a maps application executable on the user device 106-*a*. In this example, the system 300-*a* may identify a relationship between the user's physiological data and the geographical position/latitude of the user 102-*a*, and may display instructions (e.g., via a GUI of the user device 106-*a*) for adjusting behavioral characteristics of the user 102-*a* based on the geographical position/latitude and/or identified relationships. For instance, the system 300-*a* may determine that the user 102-*a* is at a high latitude that receives little sunlight throughout the course of a calendar day, and may identify a relationship between the user's physiological data and the level of sunlight experienced at the user's latitude. In this example, the system 300-*a* may display instructions for the user 102-*a* to adjust a quantity of sunlight they receive (e.g., instructions to go outside more frequently), messages indicating recommended levels of daily sunlight, and/or instructions to take actions to account for the low levels of sunlight (e.g., take vitamin D supplements). By way of another example, the system 300-*a* may determine an altitude of the user's location, and determine a relationship between changing altitudes and the user's physiological data, such as SpO2 levels (e.g., user's SpO2 levels decrease with increasing altitude).

In some aspects, the system 300-*a* may also evaluate characteristic associated with the user's surrounding environment (e.g., based on the user's geographical location), and may determine how the characteristics of the user's surrounding environment affect the user's physiological data. For example, the system 300-*a* may determine information about whether the user is in a crowded or isolated location (e.g., in a city or in a remote location), safety issues around the user's location (e.g., any known security issues in the area that may affect the user's physiological data), and the like. Such information may be retrieved via the user device 106, applications executable on the user device 106, and the like.

In some implementations, by leveraging data collected via other external devices 305 (e.g., user devices 106, charging device 305-a, smart device 305-b), techniques described herein may be used to facilitate a form of "contact tracing" between users 102. In particular, wireless connections between wearable devices 104 and/or user devices 106 associated with a user 102, and electronic devices associated with other users 102, may be used to identify potential interactions between users 102, that may then be used to provide further insight regarding relationships between the user 102 and their surrounding environment.

For example, referring to system 300-b, a first user 102-b and a second user 102-c may be associated with wearable devices 104-b, 104-c and user devices 106-b, 106-c, respectively. In this example, the wireless devices associated with the first user 102-b (e.g., user device 106-b may establish wireless connections (e.g., Bluetooth connections) with the wireless devices associated with the second user 102-c (e.g., user device 106-c) when the users 102-b, 102-c come within some distance or proximity of one another. In this regard, in this example, the user devices 106-b, 106-c may serve as "external devices" that collect additional data used to evaluate relationships between the physiological data associated with the users 102-b, 102-c and their surrounding environments.

Continuing with the same example, the system 300-b (e.g., user device 106-b, user device 106-c, server 110-b may identify a positional relationship between a first position of the first user 102-b and a second position of the second user 102-c based on the data associated with the wireless connection between the user devices 106-b, 106-c. In other words, the system 300-b may determine that the first user 102-b is likely positioned close to the second user 106-c based on the wireless connection (e.g., Bluetooth connection) that was established between the user devices 106-b, 106-c, and may therefore identify a potential interaction between the first user 106-b and the second user 106-c based on the positional relationship.

The system 300-b may be configured to identify a potential interaction between the first user 102-b and the second user 102-c based on the identified positional relationship between the users 102. For example, in cases where the system 300-b identifies that the users 102-b, 102-c were positioned close to one another for some threshold period of time, the system 300-b may identify that the users 102-b and 102-c likely interacted with one another, and may therefore identify a potential interaction between the users 102. In some aspects, the server 110-b may be configured to maintain data associated with potential interactions between users 102 of the system 300-b in order to perform a contact tracing between users 102. In some aspects, data associated with potential interactions between users 102 may be used to provide tailored messaging and guidance, such as messages indicating that a particular user 102 has been exposed to COVID and should quarantine.

In this example, the system 300-b may be configured to identify one or more characteristics associated with the potential interaction between the users 102-b, 102-c based on physiological data collected via the wearable device 104-b. That is, physiological data collected during/proximate to the potential interaction may be used to evaluate characteristics of the interaction, such as whether the potential interaction between the users 102-b and 102-c is indicative of a positive interaction, a negative interaction, or a neutral interaction. In other words, the system 300-b may utilize acquired physiological data to determine what kind of physiological effect the potential interaction had on the first user 102-b, such as whether the potential interaction made the user 102-b happy, sad, anxious, etc.

In some implementations, the systems 300-a, 300-b may enable the users 102 to engage with respective components of the respective systems 300 (e.g., wearable application 250) using voice-enabled interactions. For example, the user may be able to use to use voice commands to trigger one or more components of the system 300 (e.g., user device 106, external device 305, etc.) to read the user's scores (e.g., Sleep Score, Readiness Score, Activity Score) out loud. Such voice-enabled capability may enable the user 102 to reduce their screen time and/or blue light exposure. Moreover, such voice enabled capabilities may improve access and functionality of the system 300 with respect to blind users 102. In some cases, an external device 305, such as a virtual assistant device, may be configured to interface with the wearable application 250 so that the virtual assistant device is able to retrieve information from the wearable application 250 in response to voice commands. By way of another example, the user 102 may be able to use voice commands to start/stop workouts and/or add tags that may be used by the system 300 to further analyze and evaluate physiological data collected by the wearable device 104. Tags that may be added using voice commands may include, but are not limited to, alcohol/caffeine consumption, stress or anxiety, relaxation, and the like.

Figure 4:
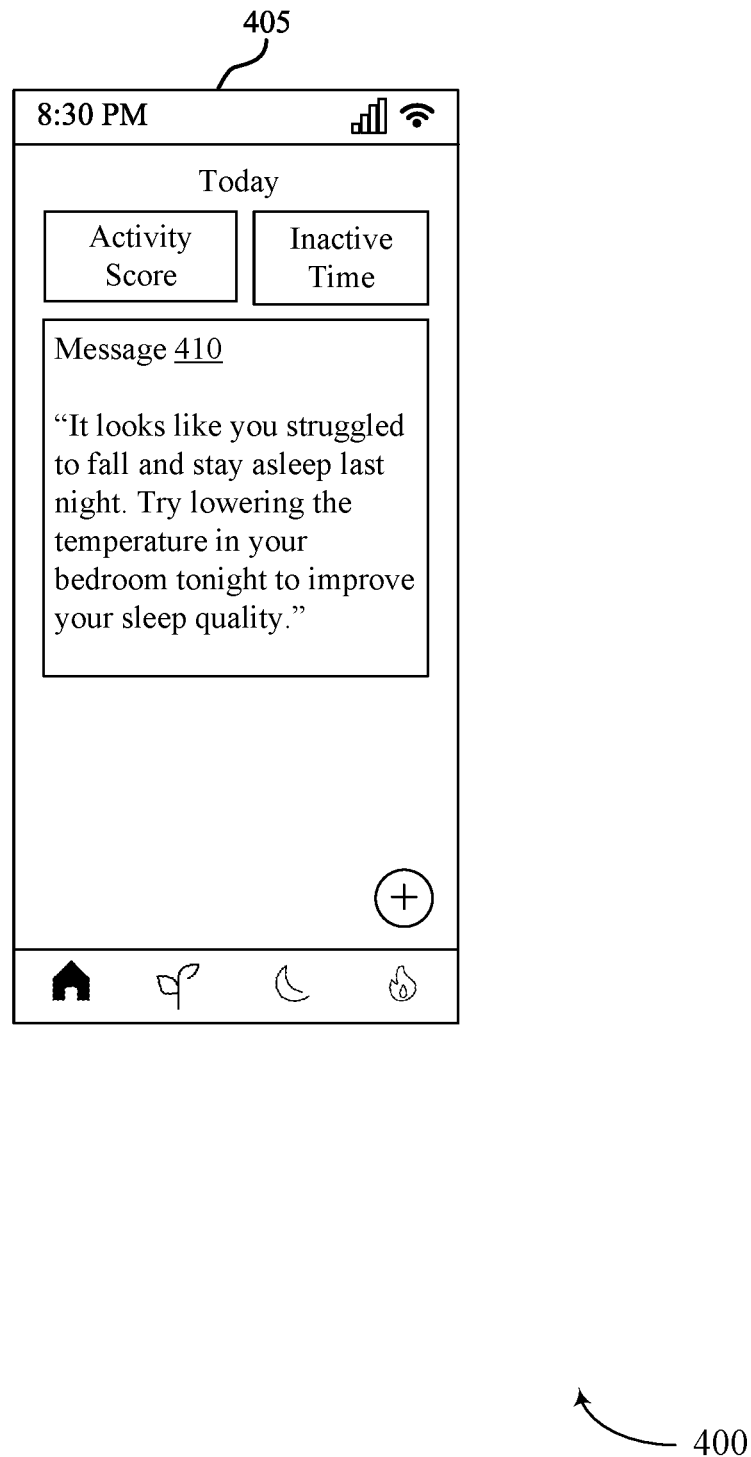
FIG. 4 illustrates an example of a graphical user interface (GUI) that supports techniques for leveraging data collected by wearable devices and additional devices in accordance with aspects of the present disclosure.

FIG. 4 illustrates an example of a GUI 400 that supports techniques for leveraging data collected by wearable devices and additional devices in accordance with aspects of the present disclosure. The GUI 400 may implement, or be implemented by, aspects of the system 100, system 200, systems 300-a, 300-b, or any combination thereof. For example, the GUI 400 may include an example of the GUI 275 included within the user device 106 illustrated in FIG. 2.

The GUI 400 illustrates an application page 405 that may be displayed to the user via the GUI 400 (e.g., GUI 275 illustrated in FIG. 2). The servers 110 of systems 100, 200, 300-a, 300-b may cause the GUI 400 of the user device 106 (e.g., mobile device) to display a message 410 associated with relationships identified between physiological data associated with the user and characteristics associated with a surrounding environment of the user.

For example, based on temperature data collected via the charging device 305-a, the system 300-a may determine that the user 102-a receives poor sleep when the temperature of the user's room raises above 71° F., and may display the message 410 via application page 405 that indicates the identified relationship. Additionally, or alternatively, the application page 405 may display messages or other guidance that instruct the user to selectively adjust characteristics of their surrounding environment. For example, continuing with the same example, the system 300-a may display a message 410 (e.g., via the application page 405) that instructs the user to lower the temperature in their bedroom to less than 71° F. in order to achieve better sleep. In other cases, the message 410 may include instructions for adjusting a sleep schedule for the user based on the identified relationships between the user's physiological data and their surrounding environment.

In some implementations, techniques described herein may be used to leverage data collected via external devices (e.g., user device 106, external devices 305) to identify positional relationships between a user and other devices, positional relationships between the user and other user, and the like. In such cases, the GUI 400 illustrated in FIG. 4 may be configured to display messages 410 associated with the identified positional relationships.

For example, upon determining a positional relationship that indicates the user 102 is likely in their kitchen, the system may cause the user device 106 to display a message 410 via application page 405 that reminds the user 102 to take their vitamins that are likely stored in the kitchen. In this regard, aspects of the present disclosure may be used to provide more tailored, target guidance/messaging to the user based on their position, that may increase the likelihood that the user will positively act in accordance with (e.g., in response to) the guidance/messaging.

Figure 5:
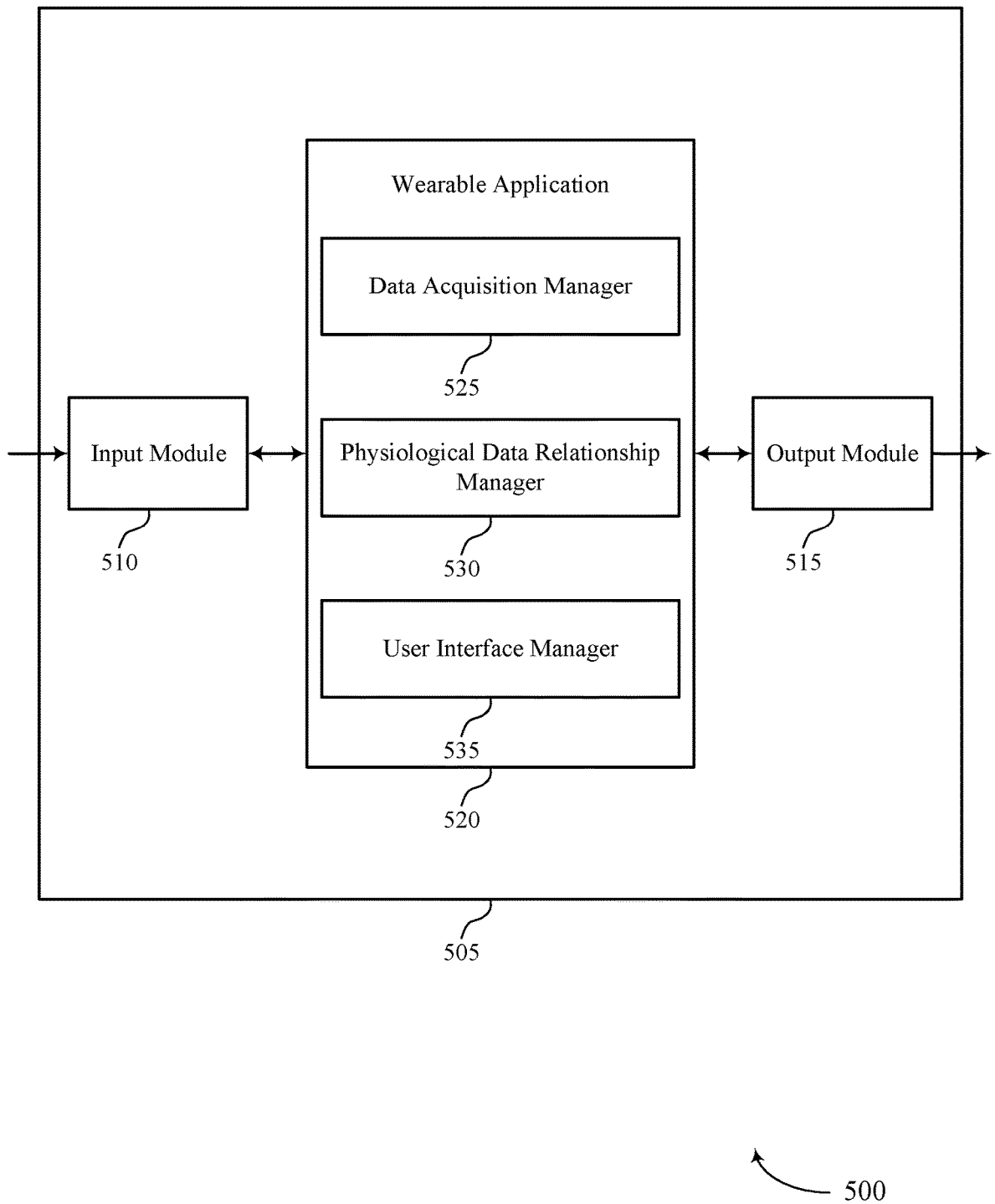
FIG. 5 shows a block diagram of an apparatus that supports techniques for leveraging data collected by wearable devices and additional devices in accordance with aspects of the present disclosure.

FIG. 5 shows a block diagram 500 of a device 505 that supports techniques for leveraging data collected by wearable devices and additional devices in accordance with aspects of the present disclosure. The device 505 may include an input module 510, an output module 515, and a wearable application 520. The device 505 may also include a processor. Each of these components may be in communication with one another (e.g., via one or more buses).

The input module 510 may provide a means for receiving information such as packets, user data, control information, or any combination thereof associated with various information channels (e.g., control channels, data channels, information channels related to illness detection techniques). Information may be passed on to other components of the device 505. The input module 510 may utilize a single antenna or a set of multiple antennas.

The output module 515 may provide a means for transmitting signals generated by other components of the device 505. For example, the output module 515 may transmit information such as packets, user data, control information, or any combination thereof associated with various information channels (e.g., control channels, data channels, information channels related to illness detection techniques). In some examples, the output module 515 may be co-located with the input module 510 in a transceiver module. The output module 515 may utilize a single antenna or a set of multiple antennas.

For example, the wearable application 520 may include a data acquisition manager 525, a physiological data relationship manager 530, a user interface manager 535, or any combination thereof. In some examples, the wearable application 520, or various components thereof, may be configured to perform various operations (e.g., receiving, monitoring, transmitting) using or otherwise in cooperation with the input module 510, the output module 515, or both. For example, the wearable application 520 may receive information from the input module 510, send information to the output module 515, or be integrated in combination with the input module 510, the output module 515, or both to receive information, transmit information, or perform various other operations as described herein.

The data acquisition manager 525 may be configured as or otherwise support a means for receiving physiological data associated with a user from a wearable device. The data acquisition manager 525 may be configured as or otherwise support a means for receiving additional data from an external device different from the wearable device, the additional data comprising at least data associated with one or more characteristics of an environment associated with the user. The physiological data relationship manager 530 may be configured as or otherwise support a means for identifying one or more relationships between the collected physiological data and the one or more characteristics of the environment associated with the user. The user interface manager 535 may be configured as or otherwise support a means for causing a GUI of a user device to display an indication of the one or more relationships, a message associated with the one or more relationships, or both.

Figure 6:
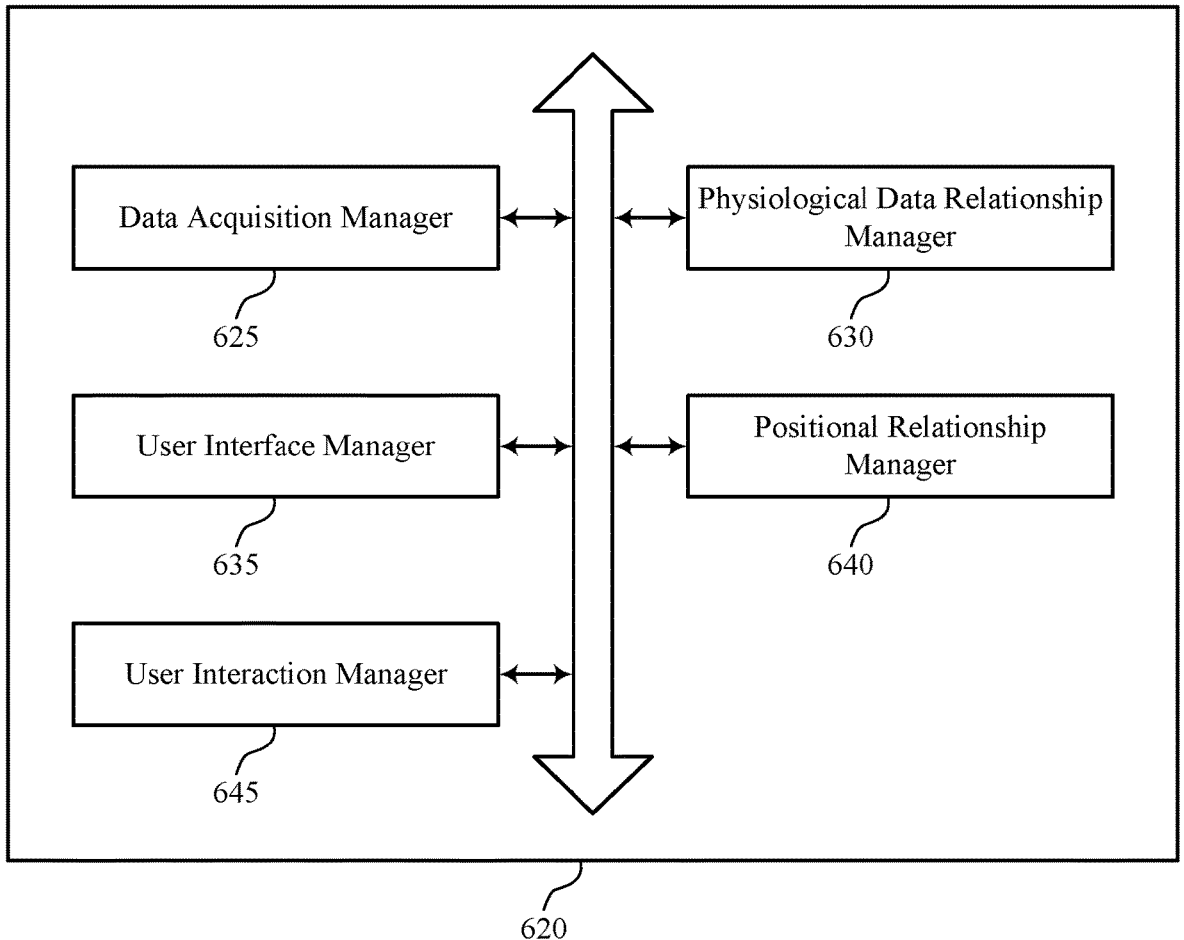
FIG. 6 shows a block diagram of a wearable application that supports techniques for leveraging data collected by wearable devices and additional devices in accordance with aspects of the present disclosure.

FIG. 6 shows a block diagram 600 of a wearable application 620 that supports techniques for leveraging data collected by wearable devices and additional devices in accordance with aspects of the present disclosure. The wearable application 620 may be an example of aspects of a wearable application or a wearable application 520, or both, as described herein. The wearable application 620, or various components thereof, may be an example of means for performing various aspects of techniques for leveraging data collected by wearable devices and additional devices as described herein. For example, the wearable application 620 may include a data acquisition manager 625, a physiological data relationship manager 630, a user interface manager 635, a positional relationship manager 640, a user interaction manager 645, or any combination thereof. Each of these components may communicate, directly or indirectly, with one another (e.g., via one or more buses).

The data acquisition manager 625 may be configured as or otherwise support a means for receiving physiological data associated with a user from a wearable device. In some examples, the data acquisition manager 625 may be configured as or otherwise support a means for receiving additional data from an external device different from the wearable device, the additional data comprising at least data associated with one or more characteristics of an environment associated with the user. The physiological data relationship manager 630 may be configured as or otherwise support a means for identifying one or more relationships between the collected physiological data and the one or more characteristics of the environment associated with the user. The user interface manager 635 may be configured as or otherwise support a means for causing a GUI of a user device to display an indication of the one or more relationships, a message associated with the one or more relationships, or both.

In some examples, one or more characteristics of the environment comprise a temperature, a noise level, an ambient light level, a humidity level, an air quality metric, an air pressure metric, or any combination thereof.

In some examples, to support causing the GUI of the user device to display the message associated with the one or more relationships, the user interface manager 635 may be configured as or otherwise support a means for causing the GUI to display instructions for selectively adjusting the one or more characteristics of the environment associated with the user.

In some examples, the positional relationship manager 640 may be configured as or otherwise support a means for identifying a positional relationship between a first position of the user and a second position of the external device based at least in part on the physiological data, the additional data, or both. In some examples, the user interface manager 635 may be configured as or otherwise support a means for causing the GUI of the user device to display a message based at least in part on the positional relationship, wherein the message is associated with the second position of the external device.

In some examples, the additional data further comprises data associated with one or more wireless connections between the wearable device and the external device, between the user device and the external device, or both. In some examples, identifying the positional relationship between the first position of the user and the second position of the external device is based at least in part on the data associated with the one or more wireless connections.

In some examples, the external device comprises the user device, and the positional relationship manager 640 may be configured as or otherwise support a means for identifying a positional relationship between a first position of the user and a second position of the second user based at least in part on the physiological data, the additional data, or both. In some examples, the external device comprises the user device, and the user interaction manager 645 may be configured as or otherwise support a means for identifying a potential interaction between the user and the second user based at least in part on the positional relationship.

In some examples, the additional data further comprises data associated with one or more wireless connections between the wearable device and the external device, between the user device and the external device, or both. In some examples, identifying the positional relationship, identifying the potential interaction, or both, is based at least in part on the data associated with the one or more wireless connections.

In some examples, the user interaction manager 645 may be configured as or otherwise support a means for identifying one or more characteristics associated with the potential interaction between the user and the second user based at least in part on the collected physiological data.

In some examples, the user interaction manager 645 may be configured as or otherwise support a means for classifying the potential interaction between the user and the second user as one of a positive interaction, a negative interaction, or a neutral interaction based at least in part on the collected physiological data.

In some examples, the external device comprises the user device, and the data acquisition manager 625 may be configured as or otherwise support a means for receiving the additional data from the external device, wherein the additional data comprises data associated with travel plans for the user, a time zone change, a Daylight Savings time shift, or any combination thereof. In some examples, the external device comprises the user device, and the user interface manager 635 may be configured as or otherwise support a means for causing the GUI of the user device to display instructions for adjusting one or more behavioral characteristics of the user based at least in part on the travel plans, the time zone change, the Daylight Savings time shift, or any combination thereof.

In some examples, the additional data is collected via one or more applications executable on the user device, the one or more applications comprising a calendar application, a mail application, a messaging application, a weather application, or any combination thereof. In some examples, the instructions for adjusting the one or more behavioral characteristics comprise instructions for adjusting a sleep schedule associated with the user.

In some examples, the additional data comprises information associated with a geographical position or latitude of the user, and the user interface manager 635 may be configured as or otherwise support a means for causing the GUI of the user device to display instructions for adjusting one or more behavioral characteristics of the user based at least in part on the geographical position or latitude of the user. In some examples, the instructions for adjusting the one or more behavioral characteristics comprise instructions for adjusting a quantity of sunlight received by the user.

In some examples, the external device comprises a charging device for the wearable device. In some examples, the additional data is collected via one or more sensors of the charging device. In some examples, the external device is different from the user device. In some examples, the wearable device comprises a wearable ring device. In some examples, the wearable device collects the physiological data from the user based on arterial blood flow.

Figure 7:
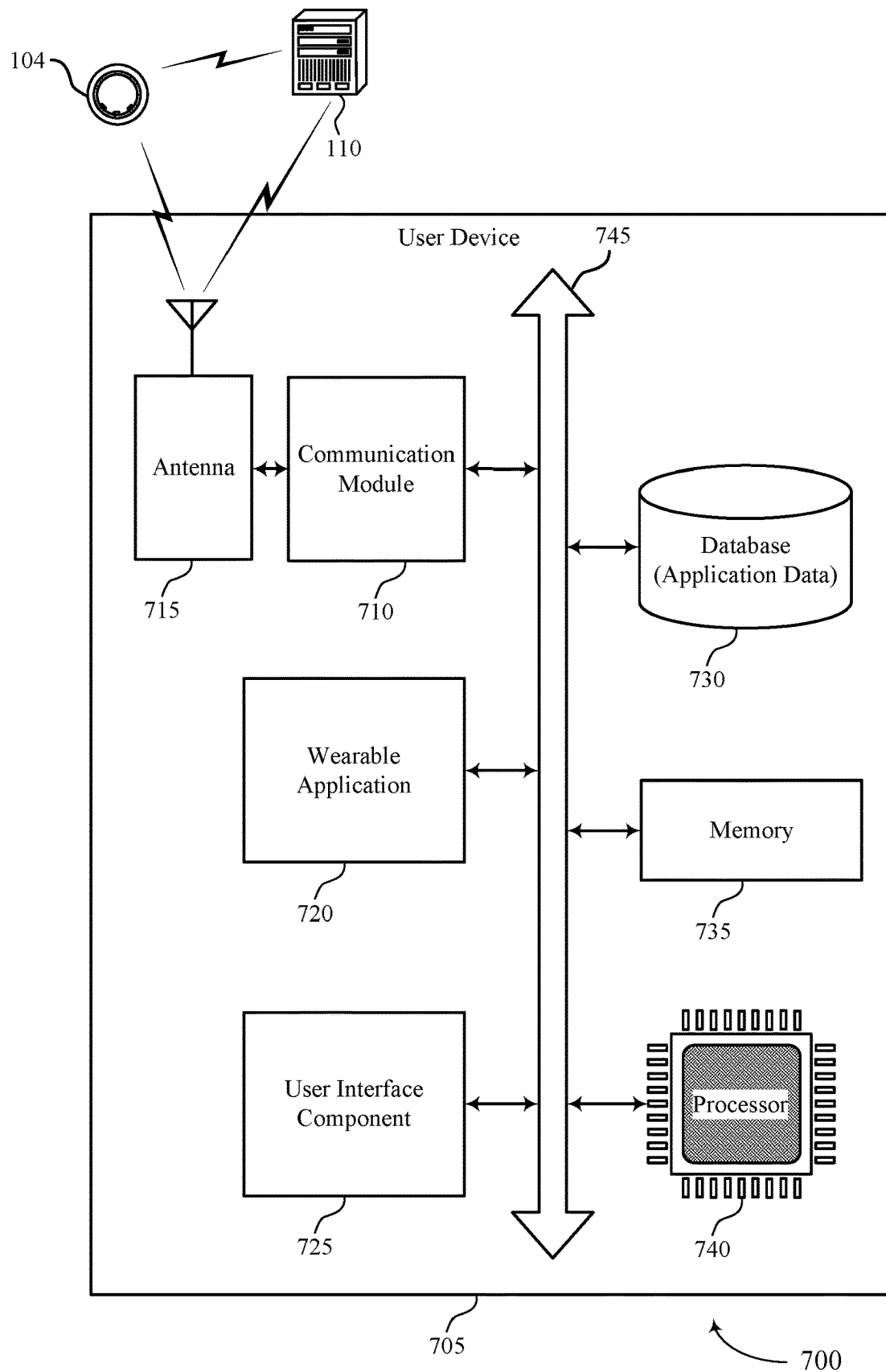
FIG. 7 shows a diagram of a system including a device that supports techniques for leveraging data collected by wearable devices and additional devices in accordance with aspects of the present disclosure.

FIG. 7 shows a diagram of a system 700 including a device 705 that supports techniques for leveraging data collected by wearable devices and additional devices in accordance with aspects of the present disclosure. The device 705 may be an example of or include the components of a device 505 as described herein. The device 705 may include an example of a user device 106, as described previously herein. The device 705 may include components for bi-directional communications including components for transmitting and receiving communications with a wearable device 104 and a server 110, such as a wearable application 720, a communication module 710, an antenna 715, a user interface component 725, a database (application data) 730, a memory 735, and a processor 740. These components may be in electronic communication or otherwise coupled (e.g., operatively, communicatively, functionally, electronically, electrically) via one or more buses (e.g., a bus 745).

The communication module 710 may manage input and output signals for the device 705 via the antenna 715. The communication module 710 may include an example of the communication module 220-*b* of the user device 106 shown and described in FIG. 2. In this regard, the communication module 710 may manage communications with the ring 104 and the server 110, as illustrated in FIG. 2. The communication module 710 may also manage peripherals not integrated into the device 705. In some cases, the communication module 710 may represent a physical connection or port to an external peripheral. In some cases, the communication module 710 may utilize an operating system such as iOS®, ANDROID®, MS-DOS®, MS-WINDOWS®, OS/2®, UNIX®, LINUX®, or another known operating system. In other cases, the communication module 710 may represent or interact with a wearable device (e.g., ring 104), modem, a keyboard, a mouse, a touchscreen, or a similar device. In some cases, the communication module 710 may be implemented as part of the processor 740. In some examples, a user may interact with the device 705 via the communication module 710, user interface component 725, or via hardware components controlled by the communication module 710.

In some cases, the device 705 may include a single antenna 715. However, in some other cases, the device 705 may have more than one antenna 715, that may be capable of concurrently transmitting or receiving multiple wireless transmissions. The communication module 710 may communicate bi-directionally, via the one or more antennas 715, wired, or wireless links as described herein. For example, the communication module 710 may represent a wireless transceiver and may communicate bi-directionally with another wireless transceiver. The communication module 710 may also include a modem to modulate the packets, to provide the modulated packets to one or more antennas 715 for transmission, and to demodulate packets received from the one or more antennas 715.

The user interface component 725 may manage data storage and processing in a database 730. In some cases, a user may interact with the user interface component 725. In other cases, the user interface component 725 may operate automatically without user interaction. The database 730 may be an example of a single database, a distributed database, multiple distributed databases, a data store, a data lake, or an emergency backup database.

The memory 735 may include RAM and ROM. The memory 735 may store computer-readable, computer-executable software including instructions that, when executed, cause the processor 740 to perform various functions described herein. In some cases, the memory 735 may contain, among other things, a BIOS that may control basic hardware or software operation such as the interaction with peripheral components or devices.

The processor 740 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 740 may be configured to operate a memory array using a memory controller. In other cases, a memory controller may be integrated into the processor 740. The processor 740 may be configured to execute computer-readable instructions stored in a memory 735 to perform various functions (e.g., functions or tasks supporting a method and system for sleep staging algorithms).

For example, the wearable application 720 may be configured as or otherwise support a means for receiving physiological data associated with a user from a wearable device. The wearable application 720 may be configured as or otherwise support a means for receiving additional data from an external device different from the wearable device, the additional data comprising at least data associated with one or more characteristics of an environment associated with the user. The wearable application 720 may be configured as or otherwise support a means for identifying one or more relationships between the collected physiological data and the one or more characteristics of the environment associated with the user. The wearable application 720 may be configured as or otherwise support a means for causing a GUI of a user device to display an indication of the one or more relationships, a message associated with the one or more relationships, or both.

The wearable application 720 may include an application (e.g., "app"), program, software, or other component that is configured to facilitate communications with a ring 104, server 110, other user devices 106, and the like. For example, the wearable application 720 may include an application executable on a user device 106 that is configured to receive data (e.g., physiological data) from a ring 104, perform processing operations on the received data, transmit and receive data with the servers 110, and cause presentation of data to a user 102.

Figure 8:
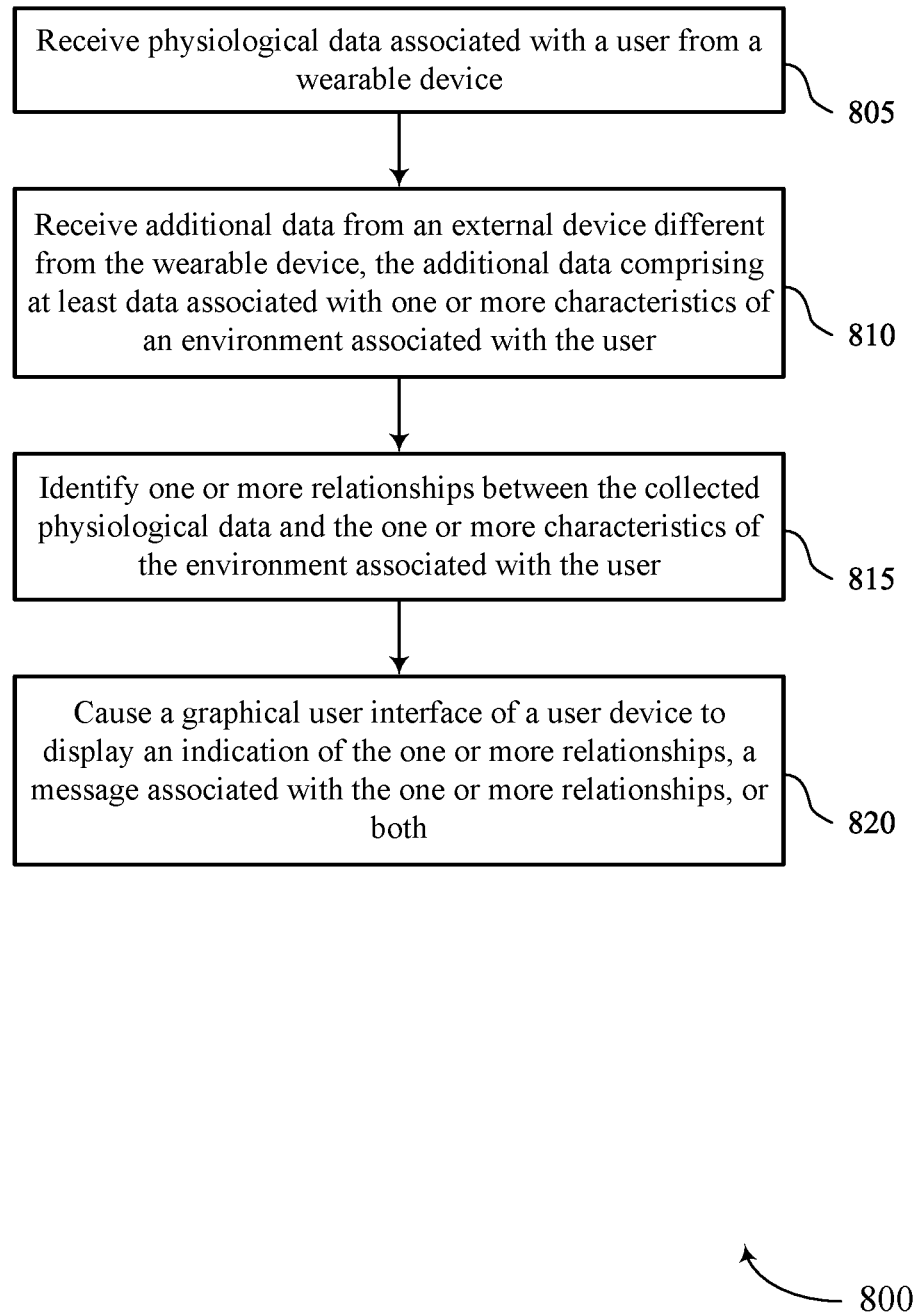
FIGS. 8 through 10 show flowcharts illustrating methods that support techniques for leveraging data collected by wearable devices and additional devices in accordance with aspects of the present disclosure.

FIG. 8 shows a flowchart illustrating a method 800 that supports techniques for leveraging data collected by wearable devices and additional devices in accordance with aspects of the present disclosure. The operations of the method 800 may be implemented by a user device or its components as described herein. For example, the operations of the method 800 may be performed by a user device as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 805, the method may include receiving physiological data associated with a user from a wearable device. The operations of 805 may be performed in accordance with examples as disclosed herein. In some examples, aspects of the operations of 805 may be performed by a data acquisition manager 625 as described with reference to FIG. 6.

At 810, the method may include receiving additional data from an external device different from the wearable device, the additional data comprising at least data associated with one or more characteristics of an environment associated with the user. The operations of 810 may be performed in accordance with examples as disclosed herein. In some examples, aspects of the operations of 810 may be performed by a data acquisition manager 625 as described with reference to FIG. 6.

At 815, the method may include identifying one or more relationships between the collected physiological data and the one or more characteristics of the environment associated with the user. The operations of 815 may be performed in accordance with examples as disclosed herein. In some examples, aspects of the operations of 815 may be performed by a physiological data relationship manager 630 as described with reference to FIG. 6.

At 820, the method may include causing a GUI of a user device to display an indication of the one or more relationships, a message associated with the one or more relationships, or both. The operations of 820 may be performed in accordance with examples as disclosed herein. In some examples, aspects of the operations of 820 may be performed by a user interface manager 635 as described with reference to FIG. 6.

Figure 9:
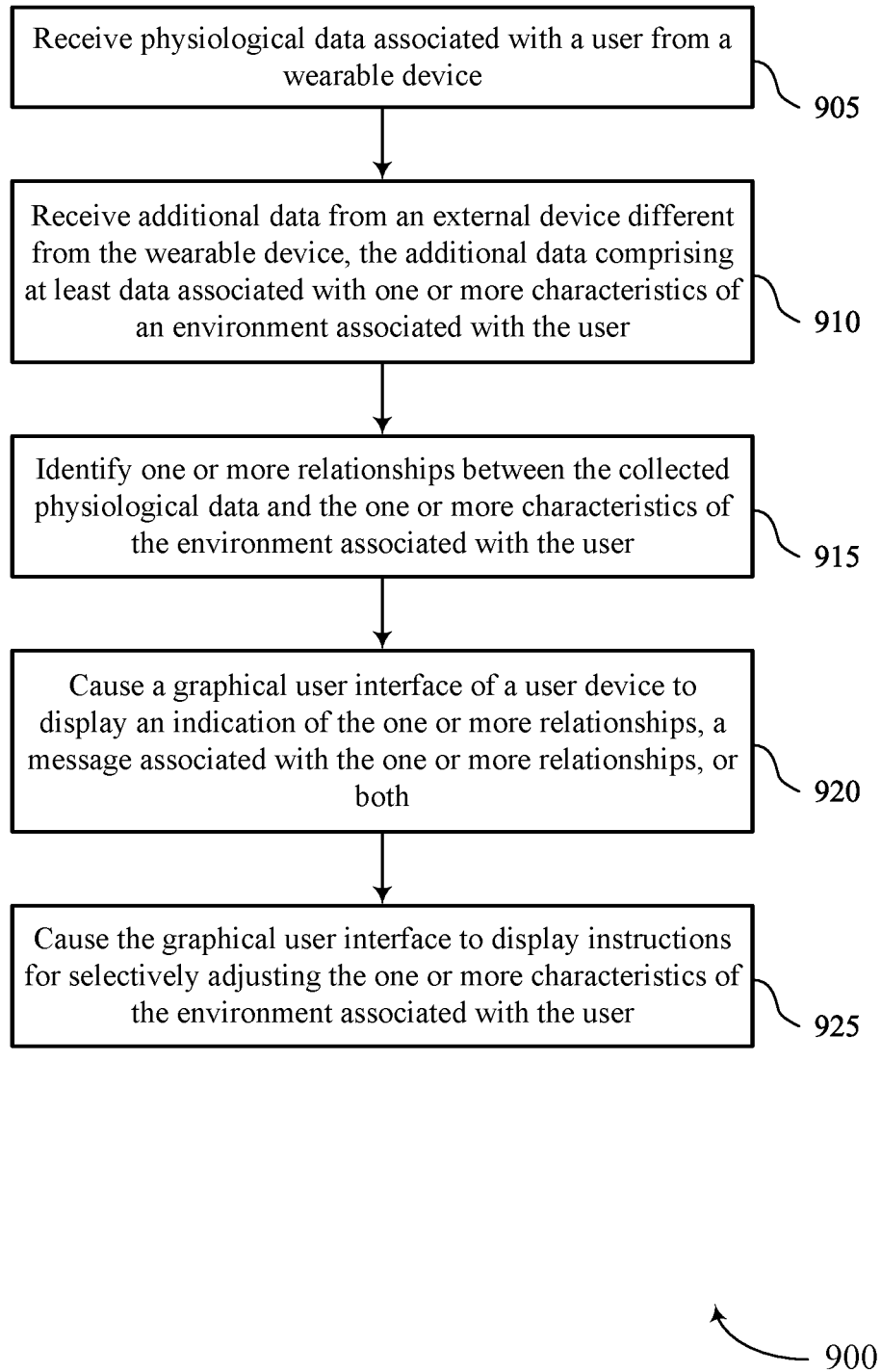

FIG. 9 shows a flowchart illustrating a method 900 that supports techniques for leveraging data collected by wearable devices and additional devices in accordance with aspects of the present disclosure. The operations of the method 900 may be implemented by a user device or its components as described herein. For example, the operations of the method 900 may be performed by a user device as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 905, the method may include receiving physiological data associated with a user from a wearable device. The operations of 905 may be performed in accordance with examples as disclosed herein. In some examples, aspects of the operations of 905 may be performed by a data acquisition manager 625 as described with reference to FIG. 6.

At 910, the method may include receiving additional data from an external device different from the wearable device, the additional data comprising at least data associated with one or more characteristics of an environment associated with the user. The operations of 910 may be performed in accordance with examples as disclosed herein. In some examples, aspects of the operations of 910 may be performed by a data acquisition manager 625 as described with reference to FIG. 6.

At 915, the method may include identifying one or more relationships between the collected physiological data and the one or more characteristics of the environment associated with the user. The operations of 915 may be performed in accordance with examples as disclosed herein. In some examples, aspects of the operations of 915 may be performed by a physiological data relationship manager 630 as described with reference to FIG. 6.

At 920, the method may include causing a GUI of a user device to display an indication of the one or more relationships, a message associated with the one or more relationships, or both. The operations of 920 may be performed in accordance with examples as disclosed herein. In some examples, aspects of the operations of 920 may be performed by a user interface manager 635 as described with reference to FIG. 6.

At 925, the method may include causing the GUI to display instructions for selectively adjusting the one or more characteristics of the environment associated with the user. The operations of 925 may be performed in accordance with examples as disclosed herein. In some examples, aspects of the operations of 925 may be performed by a user interface manager 635 as described with reference to FIG. 6.

Figure 10:
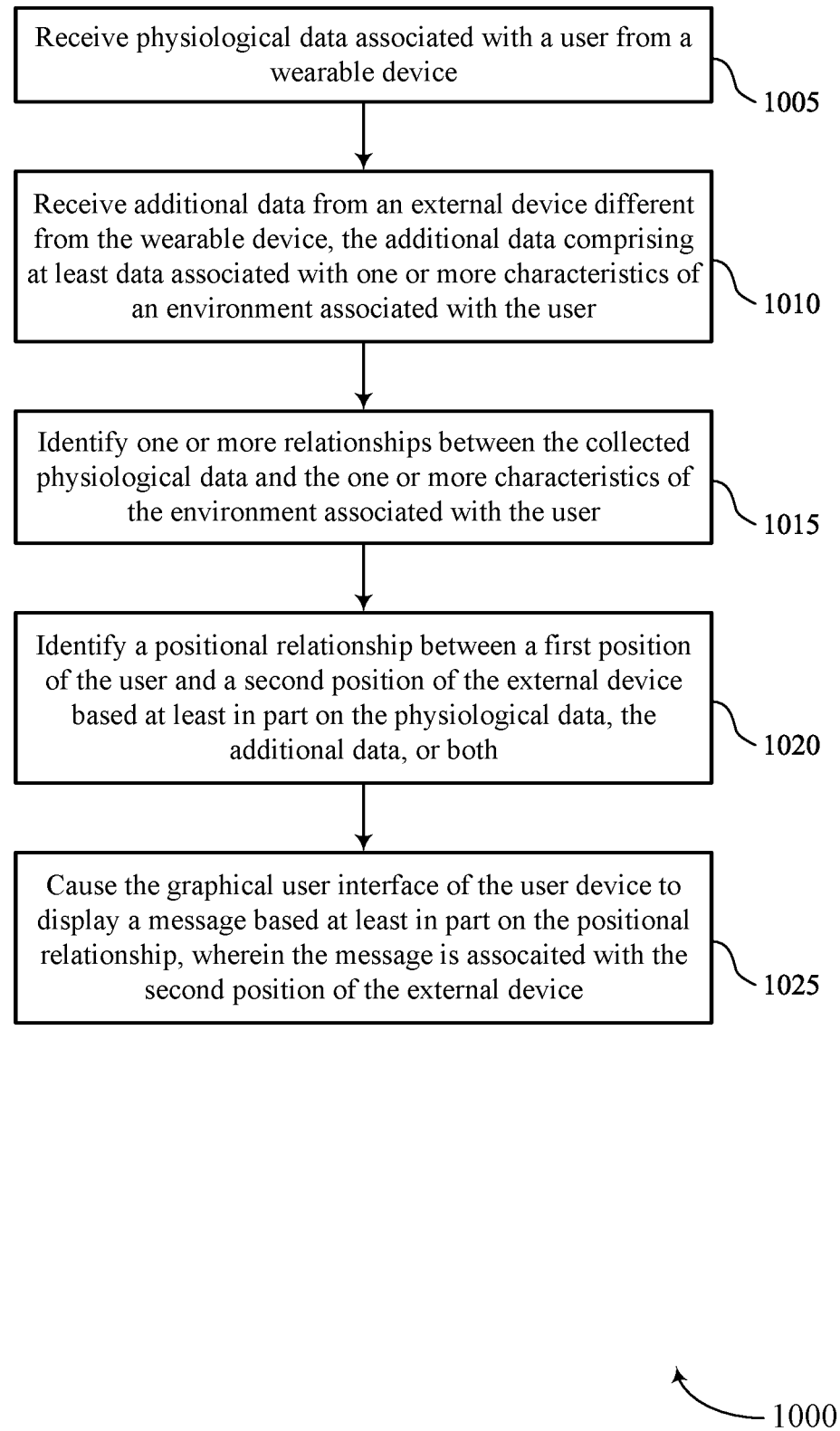

FIG. 10 shows a flowchart illustrating a method 1000 that supports techniques for leveraging data collected by wearable devices and additional devices in accordance with aspects of the present disclosure. The operations of the method 1000 may be implemented by a user device or its components as described herein. For example, the operations of the method 1000 may be performed by a user device as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 1005, the method may include receiving physiological data associated with a user from a wearable device. The operations of 1005 may be performed in accordance with examples as disclosed herein. In some examples, aspects of the operations of 1005 may be performed by a data acquisition manager 625 as described with reference to FIG. 6.

At 1010, the method may include receiving additional data from an external device different from the wearable device, the additional data comprising at least data associated with one or more characteristics of an environment associated with the user. The operations of 1010 may be performed in accordance with examples as disclosed herein. In some examples, aspects of the operations of 1010 may be performed by a data acquisition manager 625 as described with reference to FIG. 6.

At 1015, the method may include identifying one or more relationships between the collected physiological data and the one or more characteristics of the environment associated with the user. The operations of 1015 may be performed in accordance with examples as disclosed herein. In some examples, aspects of the operations of 1015 may be performed by a physiological data relationship manager 630 as described with reference to FIG. 6.

At 1020, the method may include identifying a positional relationship between a first position of the user and a second position of the external device based at least in part on the physiological data, the additional data, or both. The operations of 1020 may be performed in accordance with examples as disclosed herein. In some examples, aspects of the operations of 1020 may be performed by a positional relationship manager 640 as described with reference to FIG. 6.

At 1025, the method may include causing the GUI of the user device to display a message based at least in part on the positional relationship, wherein the message is associated with the second position of the external device. The operations of 1025 may be performed in accordance with examples as disclosed herein. In some examples, aspects of the operations of 1025 may be performed by a user interface manager 635 as described with reference to FIG. 6.

It should be noted that the methods described above describe possible implementations, and that the operations and the steps may be rearranged or otherwise modified and that other implementations are possible. Furthermore, aspects from two or more of the methods may be combined.

A method is described. The method may include receiving physiological data associated with a user from a wearable device, receiving additional data from an external device different from the wearable device, the additional data comprising at least data associated with one or more characteristics of an environment associated with the user, identifying one or more relationships between the collected physiological data and the one or more characteristics of the environment associated with the user, and causing a GUI of a user device to display an indication of the one or more relationships, a message associated with the one or more relationships, or both.

An apparatus is described. The apparatus may include a processor, memory coupled with the processor, and instructions stored in the memory. The instructions may be executable by the processor to cause the apparatus to receive physiological data associated with a user from a wearable device, receive additional data from an external device different from the wearable device, the additional data comprising at least data associated with one or more characteristics of an environment associated with the user, identify one or more relationships between the collected physiological data and the one or more characteristics of the environment associated with the user, and cause a GUI of a user device to display an indication of the one or more relationships, a message associated with the one or more relationships, or both.

Another apparatus is described. The apparatus may include means for receiving physiological data associated with a user from a wearable device, means for receiving additional data from an external device different from the wearable device, the additional data comprising at least data associated with one or more characteristics of an environment associated with the user, means for identifying one or more relationships between the collected physiological data and the one or more characteristics of the environment associated with the user, and means for causing a GUI of a user device to display an indication of the one or more relationships, a message associated with the one or more relationships, or both.

A non-transitory computer-readable medium storing code is described. The code may include instructions executable by a processor to receive physiological data associated with a user from a wearable device, receive additional data from an external device different from the wearable device, the additional data comprising at least data associated with one or more characteristics of an environment associated with the user, identify one or more relationships between the collected physiological data and the one or more characteristics of the environment associated with the user, and cause a GUI of a user device to display an indication of the one or more relationships, a message associated with the one or more relationships, or both.

In some examples of the method, apparatuses, and non-transitory computer-readable medium described herein, one or more characteristics of the environment comprise a temperature, a noise level, an ambient light level, a humidity level, an air quality metric, an air pressure metric, or any combination thereof.

In some examples of the method, apparatuses, and non-transitory computer-readable medium described herein, causing the GUI of the user device to display the message associated with the one or more relationships may include operations, features, means, or instructions for causing the GUI to display instructions for selectively adjusting the one or more characteristics of the environment associated with the user.

Some examples of the method, apparatuses, and non-transitory computer-readable medium described herein may further include operations, features, means, or instructions for identifying a positional relationship between a first position of the user and a second position of the external device based at least in part on the physiological data, the additional data, or both and causing the GUI of the user device to display a message based at least in part on the positional relationship, wherein the message may be associated with the second position of the external device.

In some examples of the method, apparatuses, and non-transitory computer-readable medium described herein, the additional data further comprises data associated with one or more wireless connections between the wearable device and the external device, between the user device and the external device, or both and identifying the positional relationship between the first position of the user and the second position of the external device may be based at least in part on the data associated with the one or more wireless connections.

In some examples of the method, apparatuses, and non-transitory computer-readable medium described herein, the external device comprises the user device and the method, apparatuses, and non-transitory computer-readable medium may include further operations, features, means, or instructions for identifying a positional relationship between a first position of the user and a second position of the second user based at least in part on the physiological data, the additional data, or both and identifying a potential interaction between the user and the second user based at least in part on the positional relationship.

In some examples of the method, apparatuses, and non-transitory computer-readable medium described herein, the additional data further comprises data associated with one or more wireless connections between the wearable device and the external device, between the user device and the external device, or both and identifying the positional relationship, identifying the potential interaction, or both, may be based at least in part on the data associated with the one or more wireless connections.

Some examples of the method, apparatuses, and non-transitory computer-readable medium described herein may further include operations, features, means, or instructions for identifying one or more characteristics associated with the potential interaction between the user and the second user based at least in part on the collected physiological data.

Some examples of the method, apparatuses, and non-transitory computer-readable medium described herein may further include operations, features, means, or instructions for classifying the potential interaction between the user and the second user as one of a positive interaction, a negative interaction, or a neutral interaction based at least in part on the collected physiological data.

In some examples of the method, apparatuses, and non-transitory computer-readable medium described herein, the external device comprises the user device and the method, apparatuses, and non-transitory computer-readable medium may include further operations, features, means, or instructions for receiving the additional data from the external device, wherein the additional data comprises data associated with travel plans for the user, a time zone change, a Daylight Savings time shift, or any combination thereof and causing the GUI of the user device to display instructions for adjusting one or more behavioral characteristics of the user based at least in part on the travel plans, the time zone change, the Daylight Savings time shift, or any combination thereof.

In some examples of the method, apparatuses, and non-transitory computer-readable medium described herein, the additional data may be collected via one or more applications executable on the user device, the one or more applications comprising a calendar application, a mail application, a messaging application, a weather application, or any combination thereof.

In some examples of the method, apparatuses, and non-transitory computer-readable medium described herein, the instructions for adjusting the one or more behavioral characteristics comprise instructions for adjusting a sleep schedule associated with the user.

In some examples of the method, apparatuses, and non-transitory computer-readable medium described herein, the additional data comprises information associated with a geographical position or latitude of the user and the method, apparatuses, and non-transitory computer-readable medium may include further operations, features, means, or instructions for causing the GUI of the user device to display instructions for adjusting one or more behavioral characteristics of the user based at least in part on the geographical position or latitude of the user.

In some examples of the method, apparatuses, and non-transitory computer-readable medium described herein, the instructions for adjusting the one or more behavioral characteristics comprise instructions for adjusting a quantity of sunlight received by the user.

In some examples of the method, apparatuses, and non-transitory computer-readable medium described herein, the external device comprises a charging device for the wearable device and the additional data may be collected via one or more sensors of the charging device.

In some examples of the method, apparatuses, and non-transitory computer-readable medium described herein, the external device may be different from the user device.

In some examples of the method, apparatuses, and non-transitory computer-readable medium described herein, the wearable device comprises a wearable ring device.

In some examples of the method, apparatuses, and non-transitory computer-readable medium described herein, the wearable device collects the physiological data from the user based on arterial blood flow.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A system comprising:
    a wearable device configured to measure photoplethysmogram (PPG) data from a user using one or more light-emitting components and one or more light-receiving components;
    a user device communicatively coupled with the wearable device; and
    one or more processors communicatively coupled with the wearable device and the user device, the one or more processors configured to:
        receive baseline physiological data measured from the user via the wearable device during a first time interval;
        receive additional data from an external device different from the wearable device, the additional data comprising at least data associated with one or more characteristics of an environment associated with the user during the first time interval;
        identify one or more relationships between the baseline physiological data and the one or more characteristics of the environment associated with the user;
        receive additional physiological data measured from the user via the wearable device during a second time interval subsequent to the first time interval;
        identify, based at least in part on the one or more relationships, one or more physiological effects that the environment of the user had on the additional physiological data of the user during the second time interval; and
        transmit an instruction configured to cause the external device, an additional external device, or both, to selectively modify the one or more characteristics of the environment associated with the user based at least in part on the one or more physiological effects.

2. The system of claim 1, wherein the one or more characteristics of the environment comprise a temperature, a noise level, an ambient light level, a humidity level, an air quality metric, an air pressure metric, or any combination thereof.

3. The system of claim 1, wherein the one or more processors are configured to:
    cause a graphical user interface of the user device to display instructions for selectively adjusting the one or more characteristics of the environment associated with the user.

4. The system of claim 1, wherein the one or more processors are further configured to:
  identify a positional relationship between a first position of the user and a second position of the external device based at least in part on the baseline physiological data, the additional data, the additional physiological data, or any combination thereof; and
  cause a graphical user interface of the user device to display a message based at least in part on the positional relationship, wherein the message is associated with the second position of the external device.

5. The system of claim 4, wherein the additional data further comprises data associated with one or more wireless connections between the wearable device and the external device, between the user device and the external device, or both, and wherein identifying the positional relationship between the first position of the user and the second position of the external device is based at least in part on the data associated with the one or more wireless connections.

6. The system of claim 1, wherein the external device comprises the user device, a second user device associated with a second user different from the user, or both, wherein the one or more processors are further configured to:
  identify a positional relationship between a first position of the user and a second position of the second user based at least in part on the baseline physiological data, the additional data, the additional physiological data, or any combination thereof; and
  identify a potential interaction between the user and the second user based at least in part on the positional relationship.

7. The system of claim 6, wherein the additional data further comprises data associated with one or more wireless connections between the wearable device and the external device, between the user device and the external device, or both, and wherein identifying the positional relationship, identifying the potential interaction, or both, is based at least in part on the data associated with the one or more wireless connections.

8. The system of claim 6, wherein the one or more processors are further configured to:
  identify one or more characteristics associated with the potential interaction between the user and the second user based at least in part on the baseline physiological data, the additional physiological data, or both.

9. The system of claim 6, wherein the one or more processors are further configured to:
  identify the potential interaction between the user and the second user as one of a positive interaction, a negative interaction, or a neutral interaction based at least in part on the baseline physiological data.

10. The system of claim 1, wherein the external device comprises the user device, wherein the one or more processors are further configured to:
  receive the additional data from the external device, wherein the additional data comprises data associated with travel plans for the user, a time zone change, a Daylight Savings time shift, or any combination thereof; and
  cause a graphical user interface of the user device to display instructions for adjusting one or more behavioral characteristics of the user based at least in part on the travel plans, the time zone change, the Daylight Savings time shift, or any combination thereof.

11. The system of claim 10, wherein the additional data is collected via one or more applications executable on the user device, the one or more applications comprising a calendar application, a mail application, a messaging application, a weather application, a navigation application, a phone application, a fitness application, a media application, or any combination thereof.

12. The system of claim 10, wherein the instructions for adjusting the one or more behavioral characteristics comprise instructions for adjusting a sleep schedule associated with the user.

13. The system of claim 1, wherein the additional data comprises information associated with a geographical position, latitude, or altitude of the user, wherein the one or more processors are further configured to:
  cause a graphical user interface of the user device to display instructions for adjusting one or more behavioral characteristics of the user based at least in part on the geographical position, latitude, or altitude of the user.

14. The method of claim 13, wherein the instructions for adjusting the one or more behavioral characteristics comprise instructions for adjusting a quantity of sunlight received by the user.

15. The system of claim 1, wherein the external device comprises a charging device for the wearable device, and wherein the additional data is collected via one or more sensors of the charging device.

16. The system of claim 1, wherein the external device is different from the user device.

17. The system of claim 1, wherein the wearable device comprises a wearable ring device.

18. The system of claim 1, wherein the wearable device collects the baseline physiological data, the additional physiological data, or both, from the user based on arterial blood flow.

19. A method, comprising:
  receiving baseline physiological data measured from a user via a wearable device during a first time interval, the baseline physiological data comprising at least baseline photoplethysmogram (PPG) data measured from the user using one or more light-emitting components and one or more light-receiving components of the wearable device;
  receiving additional data from an external device different from the wearable device, the additional data comprising at least data associated with one or more characteristics of an environment associated with the user during the first time interval;
  identifying one or more relationships between the baseline physiological data and the one or more characteristics of the environment associated with the user;
  receiving additional physiological data measured from the user via the wearable device during a second time interval subsequent to the first time interval, the additional physiological data comprising at least additional PPG data measured from the user using the one or more light-emitting components and the one or more light-receiving components of the wearable device;
  identifying, based at least in part on the one or more relationships, one or more physiological effects that the environment of the user had on the additional physiological data of the user during the second time interval; and
  transmitting an instruction configured to cause the external device, an additional external device, or both, to selectively modify the one or more characteristics of the environment associated with the user based at least in part on the one or more physiological effects.

20. A non-transitory computer-readable medium storing code, the code comprising instructions executable by a processor to:
- receive baseline physiological data measured from a user via a wearable device during a first time interval;
- receive additional data from an external device different from the wearable device, the additional data comprising at least data associated with one or more characteristics of an environment associated with the user during the first time interval;
- identify one or more relationships between the baseline physiological data and the one or more characteristics of the environment associated with the user;
- receive additional physiological data measured from the user via the wearable device during a second time interval subsequent to the first time interval;
- identify, based at least in part on the one or more relationships, one or more physiological effects that the environment of the user had on the additional physiological data of the user during the second time interval; and
- transmit an instruction configured to cause the external device, an additional external device, or both, to selectively modify the one or more characteristics of the environment associated with the user based at least in part on the one or more physiological effects.

* * * * *